United States Patent [19]

Haruki et al.

[11] 3,997,836
[45] Dec. 14, 1976

[54] DETECTOR FOR CHROMATOGRAPHS
[75] Inventors: Tatsuro Haruki; Junichi Akiyama, both of Kyoto, Japan
[73] Assignee: Shimadzu Seisakusho Ltd., Japan
[22] Filed: Aug. 12, 1975
[21] Appl. No.: 603,929
[30] Foreign Application Priority Data Aug. 29, 1974 Japan ............................ 49-99583

[52] U.S. Cl. ................................ 324/64; 324/30 R
[51] Int. Cl.² ........................................ G01R 27/14
[58] Field of Search .................. 324/64, 30 R, 30 B
[56] References Cited
UNITED STATES PATENTS

| 3,151,052 | 9/1964 | Arthur et al. ................ 324/30 B X |
| 3,376,501 | 4/1968 | Peranio ............................ 324/30 B |
| 3,896,373 | 7/1975 | Zelby ............................ 324/64 X |

FOREIGN PATENTS OR APPLICATIONS

| 964,390 | 7/1964 | United Kingdom ............... 324/308 |
| 954,557 | 4/1964 | United Kingdom ................. 324/64 |

Primary Examiner—Stanley T. Krawczewicz
Attorney, Agent, or Firm—Fidelman, Wolffe & Waldron

[57] ABSTRACT

A detector for use in chromatographs which comprises a capillary passage through which a liquid is to be passed, a first pair of electrodes spaced a distance apart from each other axially of said passage and arranged in an electrically conductive relation to said liquid for causing electric current to flow therethrough, a second pair of electrodes spaced a distance apart from each other axially of said passage between said first pair of electrodes and arranged in electrical contact with said liquid in said passage, and means connected to said second pair of electrodes for measuring changes in the potential difference therebetween.

13 Claims, 6 Drawing Figures

TIME.

DETECTOR FOR CHROMATOGRAPHS

This invention relates to a detector for use in chromatographs.

There are known various types of detectors for use in chromatographs, such as, for example, thermal-conductivity detectors and hydrogen flame-ionization detector. The former have wide applicability but low sensitivity, while the latter have high sensitivity but narrow applicability because they can chiefly detect hydrocarbons alone.

For liquid chromatographs detectors are known which rely on absorption of ultraviolet rays by the substance to be detected, or the refractive indes thereof. Those which rely on the absorption of ultraviolet rays have high sensitivity but narrow applicability because they can detect only those substances which absorb ultraviolet rays. On the other hand, those detector which are so designed as to rely on the refractive index of the substance to be detected have wide applicability but low sensitivity.

Moreover, the conventional detectors are used exclusively in either gas chromatographs or liquid chromatographs, and none of them can be used commonly in both gas chromatographs and liquid chromatographs.

Accordingly, the primary object of the invention is to provide a detector for use in chromatographs, which is superior in both applicability and sensitivity.

Another object of the invention is to provide such a detector as aforesaid which can be used commonly in both gas chromatographs and liquid chromatographs.

Another object of the invention is to provide such a detector as aforesaid which is capable of detecting all those substances which dissolve in a solvent to have a different electrical conductivity than that of the solvent.

Another object of the invention is to provide such a detector as aforesaid which requires only a small amount of sample for detection of the sample components.

Another object of the invention is to provide such a detector as aforesaid which is relatively simple in construction, and reliable in operation.

Briefly stated, in accordance with the invention the separated sample component that has come out of a chromatographic column is dissolved in a solvent and the solution is passed through a capillary tube. With electric current flowing through the solution in the column, the sample component is detected by measuring changes in the potential gradient between two points spaced a predetermined distance appart from each other in the capillary tube.

The invention will be described in more detail with reference to the accompanying drawings, wherein the same reference symbols in different figures denote corresponding parts, and wherein;

FIG. 1 schematically shows the principle of the operation of the detector of the invention;

Figure 1:
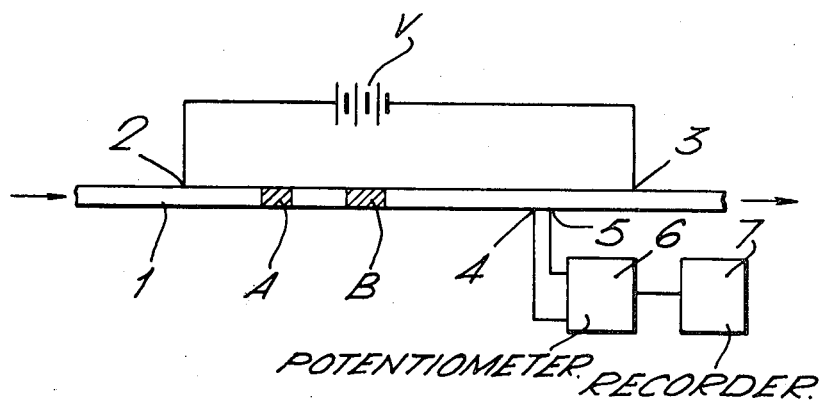

Referring in detail to the drawings, first to FIG. 1, there is shown a capillary tube 1, through which a solvent flows, with zones A and B each containing a separated sample component effluent from, say, a gas chromatographic column and disolved in the solvent. As the solvent flows in the capillary tube, the zones A and B also move carried by the flowing solvent.

The capillary tube 1 is provided with a pair of electrodes 2 and 3 spaced a suitable distance apart from each other longitudinally of the tube 1. A voltage source V is connected to the electrodes 2 and 3 so that a constant current flows through the solvent in the tube 1.

So long as the tube 1 is filled with the solvent alone between the two electrodes 2 and 3, the potential gradient is constant between the two electrodes. However, since those portions of the solvent which contain a sample component have a different electrical conductivity from that of the solvent alone, the potential gradient in the zones A and B differs from that in the adjoining areas which contain the solvent alone.

Between the electrodes 2 and 3 the capillary tube 1 is provided with a pair of detecting electrodes 4 and 5 spaced a short distance apart from each other. The electrodes 4 and 5 are connected to a potentiometer 6, which measures the potential difference between the two electrodes 4 and 5. The potential difference which changes as time passes is recorded or indicated by a recorder or indicator 7 connected to the potentiometer 6.

Figure 2:
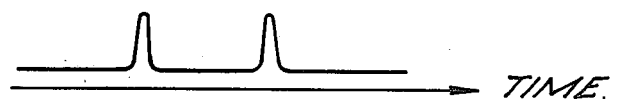
FIG. 2 is chromatogram obtained by the detector of the invention.

When the solvent alone exists between the electrodes 4 and 5, the potential difference therebetween remains constant so that the recorder 7 draws a horizontal line on the chart. When the zones A and B pass the electrodes 4 and 5, the potential difference therebetween changes so that the recorder draws peaks on the horizontal line as shown in FIG. 2. The peaks indicate the sample components contained in the zones.

Figure 3:
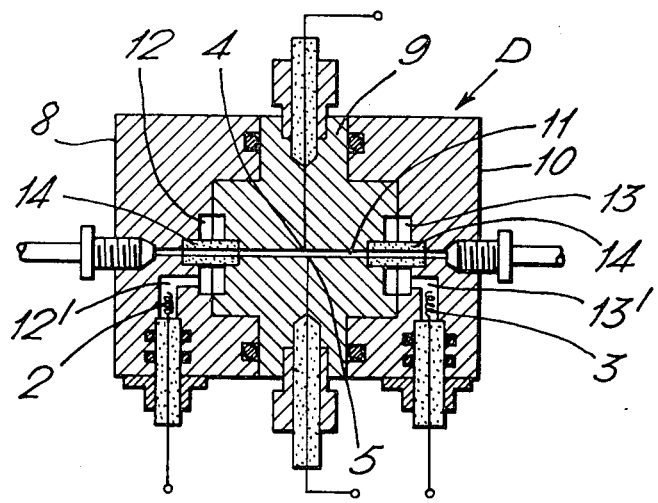
FIG. 3 is a vertical section of one embodiment of the invention.

FIG. 3 shows one example of the concrete construction of the detector of the invention. The detector comprises a housing or body D composed of three component blocks 8, 9 and 10 made of a suitable insulating material such as PTFE. The three blocks are axially arranged and put together to form the body D, with their complementarly shaped axial end faces contacting each other.

A straight axial through passage or bore 11 having a small diameter of, say 0.5 mm is formed in blocks. An annular recess encircling the passage 11 is formed in the complimentarily shaped contacting faces of the blocks so as to form an annular chamber 12, 13 about the passage 11. The passage is defined or isolated from the space in each of the chambers 12 and 13 by a tube 14 of a porous insulating material having an inner diameter of 0.5 mm and inserted into the contacting complementarily shaped end faces of the blocks so as to be aligned with the passage 11 through the blocks.

The chambers 12 and 13 are filled with an electrically conductive liquid such as electrolyte. The chambers 12 and 13 are provided with branch chambers 12' and 13', respectively, into which the electrodes 2 and 3 which are made of platinum are inserted, respectively. The porous tubes 14 may be made of PTFE or ceramic filter, which passes electric current from the electrodes 2 and 3 to the inside of the tube but prevents the solution flowing through the passage 11 from being mixed up with the electrolyte in the chambers 12 and 13. In other words, the tubes 14 provide a liquied junction between the passage 11 and the chambers 12 and 13. The tubes may be replaced by any other suitable member, such as semipermiable membrane, provided that it provides the above-mentioned liquid junction.

If the chambers 12 and 13 directly communicated with the passage 11, as the zone A or B passed the chambers 12 or 13, the sample component contained therein would be diffused into the electrolyte in the chamber so that a tailing would occur to cause two peaks to overlap each other with a resulting decrease in resolution. In accordance with the invention, this is effectively prevented by the provision of the tube 14.

The detecting electrodes 4 and 5 in FIG. 1 are shown in FIG. 3 as a pair of needle electrodes which are inserted radially into the central block 9 from the diametrically opposite sides thereof as far as their respective inner ends are exposed at the inner circumferential wall surface of the passage 11. In the illustrated embodiment the exposed ends of the needle electrodes do not project into the passage 11 but are flush with the inner surface thereof. The exposed ends of the electrodes may project into the passage 11. The exposed ends of the electrodes are spaced a predetermined distance from each other axially of the passage. The shorter the distance, the better, that is, the more quickly can the detector detect changes in the potential difference. The distance between the two detecting electrodes may range, for example, from 0.05 mm to 5 cm although this range should never be taken to limit the scope of the invention.

Figure 4:
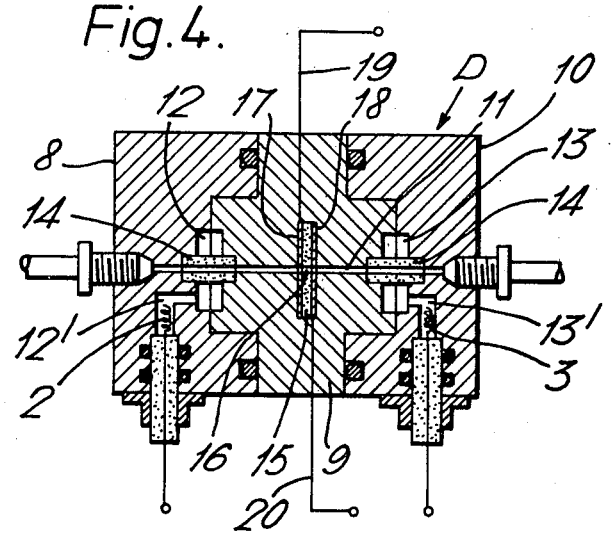
FIG. 4 is a view similar to FIG. 3 but showing another embodiment of the invention.
Figure 5:
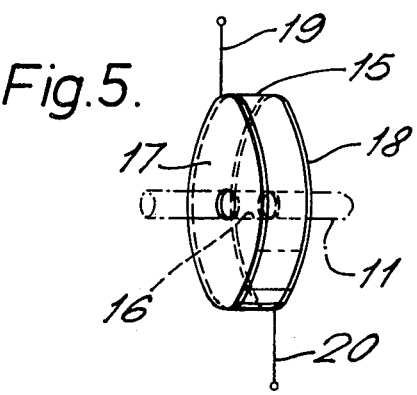
FIG. 5 is a somewhat schematic perspective view of the detecting electrodes shown in FIG. 4.

FIGS. 4 and 5 show another form of the detecting electrodes to be used in the detector of the invention. A disk 15 made of a suitable insulating material is formed with a central hole 16 of the same diameter, say, 0.5 mm, as that of the passage 11. On the opposite side surfaces of the disk 15 a thin film 17, 18 of an electrically conductive material such as platinum is formed by vacuum evaporation or any other suitable method, with a pair of leads 19 and 20 being connected to the films 17 and 18, respectively. The disk 15 with the opposite platinum films 17 and 18 is arranged in the central block 9 so that the hole 16 of the disk 15 axially coincides with and forms part of the passage 11. It will be easily seen that the two films 17 and 18 function as the detecting electrodes 4 and 5 just like the previously mentioned needle electrodes.

The electrodes 2 and 3 are connected to the constant current source V while the detecting electrodes 4 and 5 (or 17 and 18) are connected to the potentiometer 6.

If the detector is to be used as a detector for a liquid chromatograph, the outlet side of the column C of the chromatograph may simply be connected to, say, the left-hand side of the passage 11.

Figure 6:
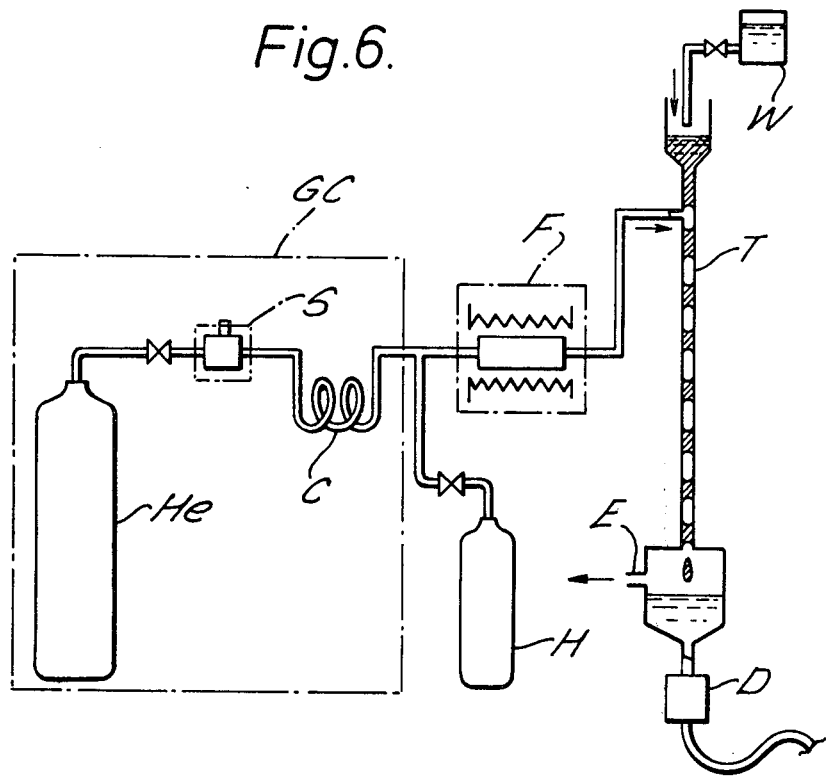
FIG. 6 is a schematic layout of a gas chromatograph which employs the detector of the invention.

FIG. 6 schematically shows the detector used as a detector for a gas chromatograph. The gas chromatograph is schematically shown as a dashed-line block GC comprising a column C, a sample introducing portion S and a bomb He containing a carrier gas such as helium. The effluent end of the column C is connecting to the inlet of a furnace F, into which a reactive gas, say, hydrogen is also introduced from a bomb H. A catalyst is placed in the furnace, where the effluent sample component from the chromatographic column C reacts with the reactive gas from the bomb H so as to be decomposed or produce a compound.

To the outlet of the furnace F there is connected an absorption tube T arranged generally vertically, with a source of water W being connected to the upper end of the tube T so that water flows down therethrough.

The effluent gas from the furnace F is introduced into the tube T at an upper end thereof and caused to flow down through the tube sc as to be discharged from an outlet E provided at the lower end of the tube. As the effluent gas bubbles down in the tube, any substance contained in the gas and originating from the sample is contacted by the water and dissolved therein. The detector D of the invention is connected to the lower end of the tube T.

If hydrogen is used as the reactive gas, any sample component containing nitrogen is converted in the furnace F to ammonia. If the sample component contains a halogen, reaction with hydrogen will produce a hydrogen halide. If oxygen is used as the reactive gas, any sulfur contained in the sample component becomes sulfur dioxide which is dissolved in water to produce ions to which the detector D is highly sensitive.

In the above embodiment, the distance between the electrodes 2 and 3 is several centimeters, but it may be shorter, for example, several millimeters or longer. In the latter case, that is, with a longer distance between the electrodes 2 and 3 and a higher voltage applied thereto, those sample components which could not be separated by a chromatograph can be separated in accordance with the different mobilities of their ions in the solvent.

The detector of the invention can detect any substance provided that it is dissolved in a solvent to present an electrical conductivity different from that of the solvent and it can be used in either a gas chromatograph or a liquid chromatograph.

The volume of the detecting portion is given as the product of the cross-sectional area of the passage 11 and the distance between the two detecting electrodes 4 and 5. In the illustrated embodiment, the volume is as small as about 0.1 $\mu l$, so that a small amount of sample component suffices for detection if it is dissolved in such a small quantity of solvent to provide an appreciable degree of concentration. The detector also has a high degree of sensitivity.

What we claim is:

1. A detector for use in a chromatograph comprising: means for defining a passage through which a liguid is to be passed; said liquid including successive separate zones, each said zone containing a separate sample component, said passage being of a size adapted to maintain said zones in separation as the liquid flows through the detector; a first pair of electrodes spaced a predetermined distance apart from each other axially of said passage; means for arranging said electrodes in an electrically conductive relation to the inside of said passage; means for impressing a voltage from a DC source across said electrodes; a second pair of electrodes spaced a predetermined short distance apart from each other axially of said passage and between said first spaced pair of electrodes, said second pair of electrodes being in electrical contact with said liquid in said passage; and means connected to said second pair of electrodes for measuring changes in the potential difference therebetween.

2. The detector of claim 1, wherein said chromatograph is a gas chromatograph, and further including means for causing the effluent from said chromatograph to be dissolved in said liquid before said liquid is introduced into said passage.

3. The detector of claim 1, wherein said chromatograph is a liquid chromatograph and said liquid is the effluent from said liquid chromatograph.

4. The detector of claim 1, wherein said liquid is a solvent.

5. The detector of claim 1, wherein said passage defining means comprises: a central block and a pair of opposite end blocks put together with their complementarily shaped end faces contacting each other; and an axial bore formed through said blocks so as to constitute said passage; and a pair of annular chambers formed in said contacting end faces so as to encircle said bore; and a member disposed in each said annular chamber so as to define and separate part of said bore from the remaining space of each said annular chamber.

6. The detector of claim 5, wherein said annular chambers are filled with electrically conductive liquid, and each of said first pair of electrodes has a portion thereof arranged in contact with said liquid in one of said annular chambers, and each said member is made of such a material as to provide a liquid junction between said passage and said chamber.

7. The detector of claim 6, wherein each said member comprises a tube having substantially the same inner diameter as that of said passage.

8. The detector of claim 7, wherein said tube is made of a porous material.

9. The detector of claim 6, wherein each said member is made of semipermeable membrane.

10. The detector of claim 5, wherein said second pair of electrodes are needle electrodes.

11. The detector of claim 10, wherein said needle electrodes are inserted into said central block as far as their inner ends are exposed at the inner wall surface of said axial bore between said pair of annular chambers so as to be in contact with said liquid in said bore, said exposed ends being spaced a predetermined relatively short distance apart from each other axially of said bore.

12. The detector of claim 5, wherein said second pair of electrodes comprise thin films of electrically conductive material formed on the opposite sides of a disk of insulating material having a central hole which constitutes part of said passage.

13. The detector of claim 1 wherein said passage is a straight, axial, capillary passage.

* * * * *